United States Patent [19]
DeSatnick et al.

[11] Patent Number: 5,899,920
[45] Date of Patent: May 4, 1999

[54] SUTURE ANCHOR ASSEMBLY AND KIT

[75] Inventors: Allen H. DeSatnick; Ella Zaslavsky, both of Marblehead, Mass.

[73] Assignee: Wright Medical Technology, Inc., Arlington, Tenn.

[21] Appl. No.: 08/799,120

[22] Filed: Feb. 11, 1997

[51] Int. Cl.$^6$ .................................................. A61B 17/04
[52] U.S. Cl. ............................... 606/232; 606/86; 606/73
[58] Field of Search .................................... 606/237, 104, 606/103, 99, 86, 73, 75, 79, 80, 187, 83–85; 623/13

[56] References Cited

U.S. PATENT DOCUMENTS

| | | | |
|---|---|---|---|
| 4,632,100 | 12/1986 | Somers et al. | 128/92 |
| 5,224,946 | 7/1993 | Hayhurst et al. | 606/232 |
| 5,466,243 | 11/1995 | Schmieding et al. | 606/232 |
| 5,534,011 | 7/1996 | Greene, Jr. et al. | 606/232 |
| 5,591,207 | 1/1997 | Coleman | 606/104 |

OTHER PUBLICATIONS

Ogden, "A New Bone Anchor for Re–Attachment of Soft Tissue and Management of Fractures and Dislocations" *Orthopedic Surgery*, Surgical Technology International III, pp. 593–602, Oct., 1994.

Rosenberg, "Endoscopic Technique For ACL Reconstruction With Pro–Trac Tibial Guide", *Acufex*, 1991.

"Statak™ Soft Tissue Attachment Device", *Zimmer*, 1994.
Bradley, "The Anchor That Holds Fast", *Linvatec*, 1994.

*Primary Examiner*—Michael Buiz
*Assistant Examiner*—Tina T. D. Pham
*Attorney, Agent, or Firm*—Lappin & Kusmer LLP

[57] ABSTRACT

A self-threading suture anchor assembly and kit includes a suture anchor having an anchor portion at one end and a drive portion with an eyelet at an opposite end, and an elongated suture threading loop with an elongated, substantially rigid gripping member attached thereto. The threading loop is collapsible, yet it maintains a loop shape. The elongated gripping member acts as a wand for manipulation of the loop. Both the threading loop and the elongated gripping member are adapted to be encased in a removable elongated sheath which extends beyond the ends of the loop and gripping member. The assembly is inserted into a cannulated shaft of a rotatable driver which includes a bone-cutting drive bit adapted for gripping the suture anchor at its drive end and for cutting into bone. The distal portion of the elongated sheath extends through a port in the shaft and is frictionally engageable with the shaft by means of an annular retaining element slidably disposed on the shaft. Removal of the driver from the anchor after installation of the anchor in a bone effects simultaneous removal of the elongated sheath from the threading loop and gripping member, which, when exposed, permit threading of a suture or section of tendon or other soft tissue through the eyelet of the suture anchor.

14 Claims, 5 Drawing Sheets

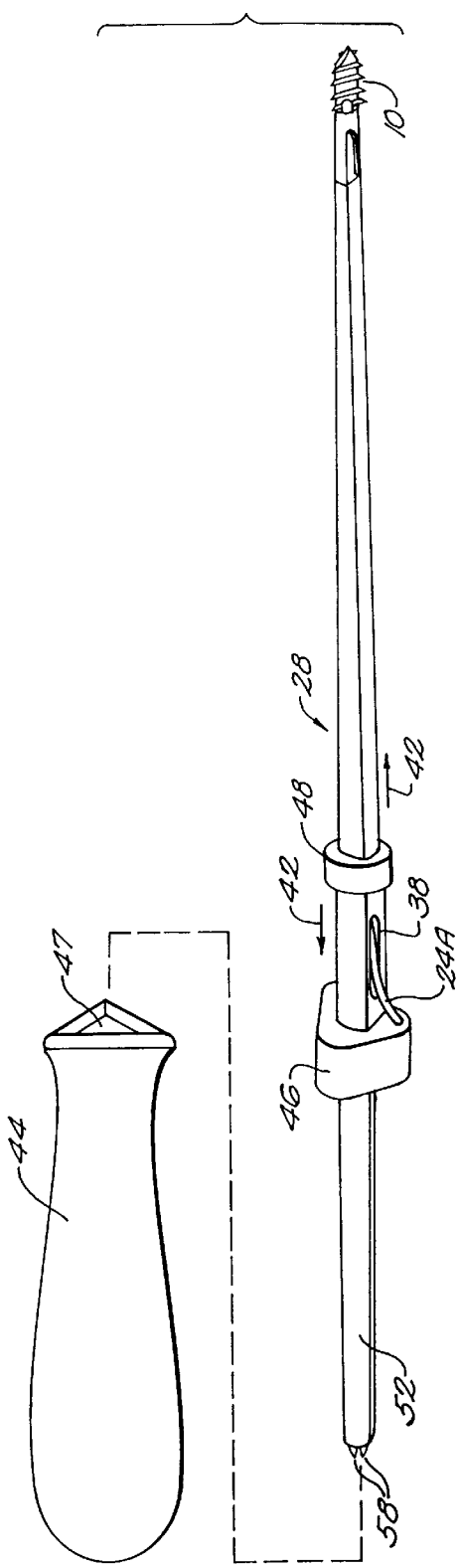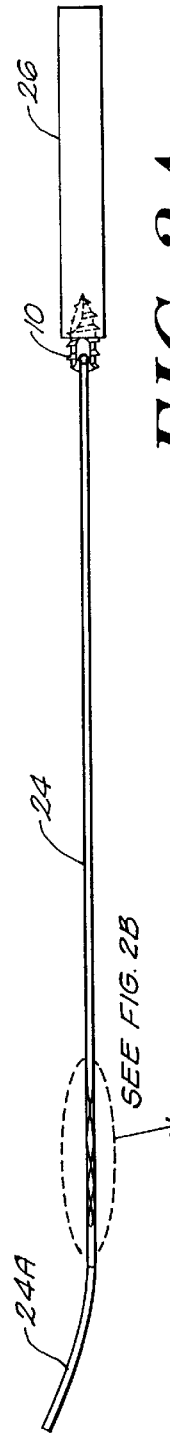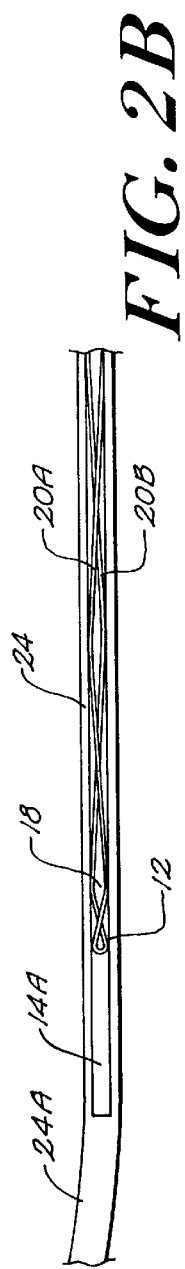

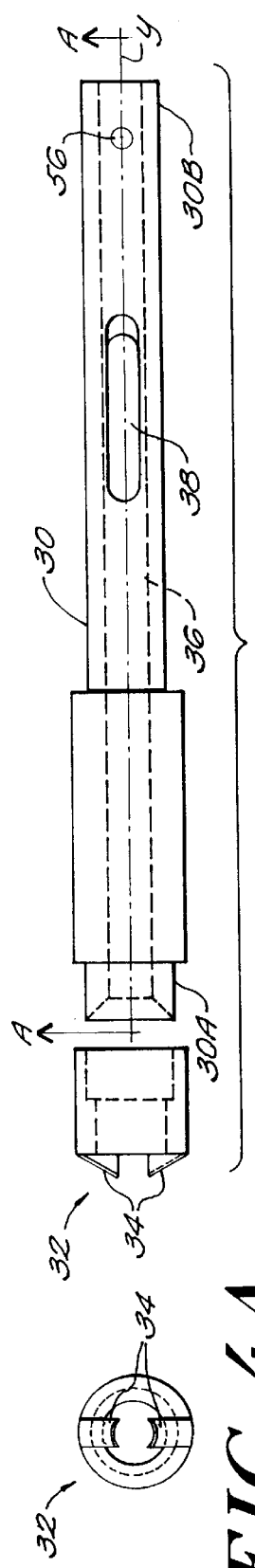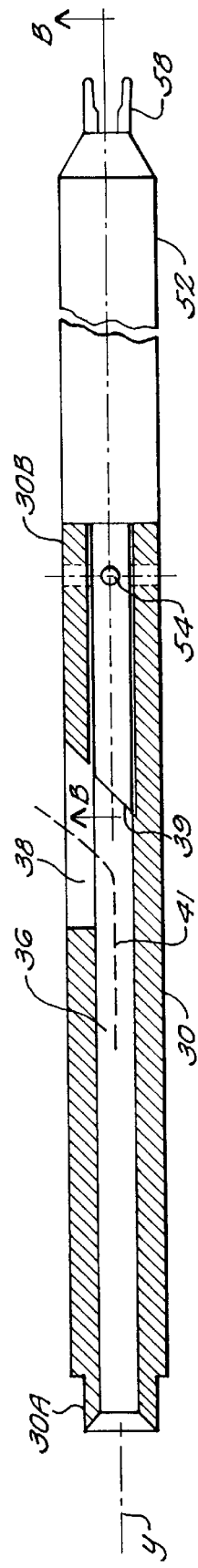
FIG. 4A
FIG. 4B
FIG. 5

> # 5,899,920

SUTURE ANCHOR ASSEMBLY AND KIT

FIELD OF THE INVENTION

The present invention relates to devices for securing soft tissue to bone, and more particularly to suture anchors and equivalent devices which include an eyelet at a proximal end for passage of a suture or soft tissue section therethrough.

BACKGROUND OF THE INVENTION

Suture anchors are widely used in surgical procedures to provide a fixture on or within a bone for attaching sutures or soft tissue segments, such as tendons, thereto. Typical suture anchors have a threaded or barbed distal end which is adapted for penetration into, and relatively secure engagement in, a bone, and an eyelet or other receptacle at a proximal end for passage of a suture or soft tissue segment therethrough.

In many applications, it is useful to be able to install a suture anchor in a bone and then thread a suture through the eyelet of the installed anchor. However, this is difficult to accomplish because of the relatively small size of the suture anchor and the eyelet through which the suture must pass, the fineness and limpness of the suture material, and the confined surgical space at the site of installation.

U.S. Pat. No. 5,534,011 to Greene, Jr. et al. discloses a method and apparatus for threading a suture through the exposed eyelet of a suture anchor after the anchor is installed in a bone. In the Greene, Jr. et al. method, a suture anchor is provided with a portion of a suture-engaging implement pre-installed in the eyelet of the anchor. The suture anchor with the pre-installed suture-engaging implement is driven into a bone so as to leave the eyelet and suture-engaging implement exposed. A suture is then engaged with the suture-engaging implement, which is then pulled through the eyelet to thread the suture through the eyelet. The suture-engaging implement is then disengaged from the suture.

The suture engaging implement of Greene, Jr. et al. is preferably either a thin, flexible tube of a biocompatible material with a flared end for receiving a suture therein, or a loop of a flexible, biocompatible wire. The loop or wire is attached at its ends to a metal knob or gripping member.

The Greene, Jr. et al. method and apparatus present some difficulties in threading the suture anchor after it has been installed in a bone. For example, the metal knob or gripping member is relatively small and thus does not facilitate the grasping and manipulation of the suture engaging implement. In addition, the suture-engaging implement and the attached gripping member do not necessarily fit closely together or otherwise facilitate handling and control of the suture anchor and the suture threading components.

OBJECTS OF THE INVENTION

It is therefore an object of the invention to provide a suture anchor assembly which overcomes the deficiencies of prior art suture anchors.

Another object of the invention is to provide a suture anchor assembly which permits a suture anchor to be easily threaded with a suture or a section of tendon or other soft tissue after the suture anchor is installed in a bone.

Still another object of the invention is to provide a suture anchor assembly which includes a pre-installed suture threader that can be easily manipulated.

SUMMARY OF THE INVENTION

The suture anchor assembly of the present invention provides for easy and convenient threading of a suture anchor with a suture or a section of a tendon or other soft tissue after the anchor has been installed in a bone, regardless of the size of the suture anchor and suture or tissue section used. The assembly includes a suture threading loop which is attached at one end to a rigid, elongated gripping member. The elongated gripping member acts as a wand which provides enhanced control and maneuverability of the gripping member and threading loop and permits the surgeon to thread the suture anchor from outside of the patient's body, a clear advantage in confined surgical spaces. The suture threading loop and gripping member are preferably enclosed in an elongated sheath which extends beyond the ends of the loop and gripping member. This sheathed assembly is inserted into a rotatable cannulated driver and through a sidewall port in the driver. The sheath protects the loop and the gripping member prior to and during their installation into the driver and through the eyelet of the suture anchor. By extending the end of the sheath through the sidewall port of the driver, the sheath can be easily and conveniently removed with the driver after the suture anchor is installed in a bone.

According to one aspect of the invention, a self-threading suture anchor assembly comprises:

A. a suture anchor extending along a principal axis and having an eyelet at a drive end and an anchor portion at an end opposite the drive end; and B. an elongated suture threading loop extending from two proximal loop ends through the eyelet of the suture anchor and having an elongated, substantially rigid gripping member extending from the proximal ends of the loop.

In a preferred embodiment, the loop is positionable adjacent to and alongside the gripping member. In addition, an elongated sheath is disposed around and frictionally engaged with the loop and the gripping member.

The elongated sheath extends from a point near the proximal ends of the loop and the gripping member to a point beyond the loop and the gripping member.

In a preferred embodiment, the suture threading loop is sufficiently rigid to maintain a loop shape. The loop is disposed about a void region and includes two substantially parallel leg portions extending from the void region to the gripping member. The proximal ends of the loop are secured to the elongated gripping member, preferably near a proximal end of the gripping member.

According to another aspect of the invention, a self-threading suture anchor kit is provided which comprises:

A. a self-threading suture anchor assembly, including:
  i. a suture anchor extending along a principal axis and having an eyelet at a drive end and an anchor portion at an end opposite the drive end; and
  ii. an elongated suture threading loop extending from two proximal loop ends through the eyelet of the suture anchor and having an elongated, substantially rigid gripping member extending from the proximal ends of the loop, wherein the elongated suture threading loop is positionable adjacent to and alongside the elongated gripping member and is sufficiently rigid to maintain a loop shape, and wherein the loop is disposed about a void region and includes two substantially parallel leg portions extending from the void region to the gripping member; and
  iii. an elongated sheath disposed around and frictionally engaged with the loop and the gripping member, the loop extending from a point near the proximal ends of the loop and the gripping member to a point beyond the loop and the gripping member; and B. a rotatable driver including a cannulated shaft extending along a principal axis between first and second ends, the first end being removably engageable with the drive end of the suture anchor, the cannulated shaft defining a central canal adapted for passage of the elongated sheath therethrough and including a port in a sidewall of the cannulated shaft, wherein the distance between the port and the first end of the cannulated shaft is less than the length of the elongated sheath.

The kit includes a bone-cutting drive bit which is engageable with the first end of the cannulated shaft and which includes a pair of axially extending prong-like projections which are adapted for releasable engagement with the drive end of the suture anchor and for cutting a chamfered, countersunk hole in bone.

The kit can further include an annular element disposed around the cannulated shaft between the port and the first end of the shaft. The annular element is adapted for frictional engagement with the distal portion of the elongated sheath extending from the port in the shaft to hold the sheath in place relative to the driver.

The kit can also include a handle which is adapted for releasable engagement with the second end of the cannulated shaft.

The kit can further include an anchor extractor member disposed at the second end of the cannulated shaft. The extractor member is preferably adapted for releasable engagement with the drive end of the suture anchor for removal of the suture anchor after installation in a bone. A handle which is adapted for releasable engagement with the first end of the cannulated shaft can also be included.

In a preferred embodiment, the anchor extractor member, when installed in the cannulated shaft, acts as a deflector for guiding the elongated sheath in the shaft toward the port.

These and other features of the invention will be more fully appreciated with reference to the following detailed description which is to be read in conjunction with the attached drawings.

BRIEF DESCRIPTION OF THE DRAWINGS

The invention is further described by the following description and figures, in which:

FIG. 1 is an exploded perspective view of the suture anchor assembly and kit of the present invention;

FIG. 2A is a side elevational view of the suture anchor, the suture threading loop, the elongated gripping member, and the elongated sheath;

FIG. 2B is a detail view of the suture threading loop and the elongated gripping member installed in the elongated sheath;

FIG. 4A is an axial view of a bone-cutting drive bit which is engageable with the first end of the cannulated shaft;

FIG. 4B is an exploded side elevational view of the bone-cutting drive bit of FIG. 4A and the cannulated shaft;

FIG. 5 is a sectional view of the cannulated driver of FIG. 4B along section lines A—A, including the anchor extractor member as it attaches to the second end of the cannulated driver shaft;

Like elements in the respective figures have the same reference numbers.

DETAILED DESCRIPTION OF THE PREFERRED EMBODIMENT

The self-threading suture anchor assembly and kit of the present invention are illustrated in FIG. 1, and the components of the assembly and kit are shown in greater detail in FIGS. 2–9C.

The assembly comprises a suture anchor 10, an elongated suture threading loop 12 (shown in FIGS. 2B and 3A–3B), and an elongated gripping member 14 (shown in FIGS. 2A–2B and 3A–3C) attached to the suture threading loop.

Figure 3A:
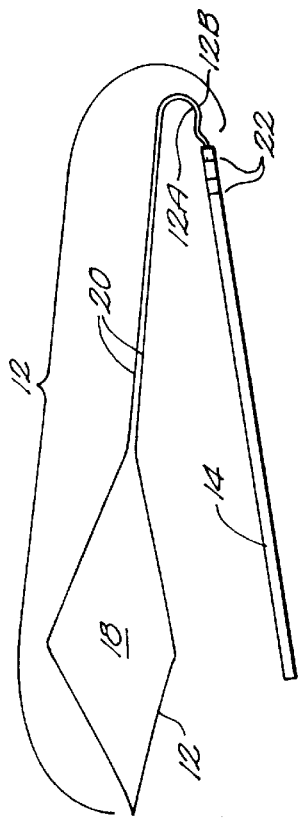
FIG. 3A is a perspective view of the suture threading loop and elongated gripping member.
Figure 3B:
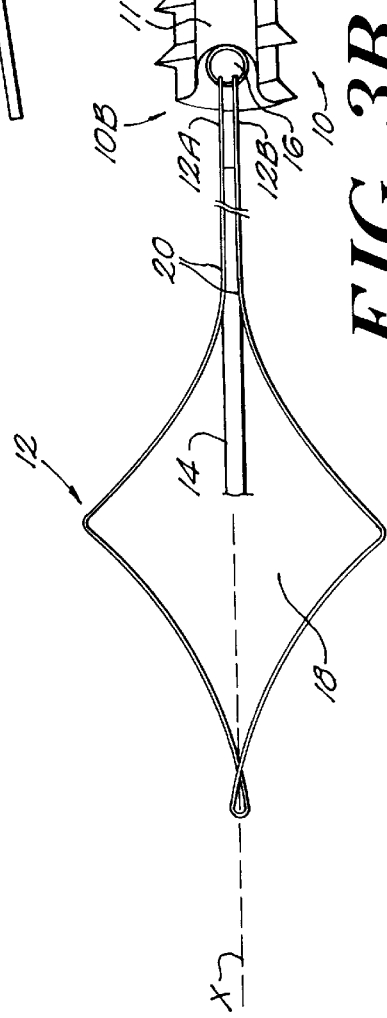
FIG. 3B is a side elevational view of the suture anchor in an anchor protecting sleeve, with the suture threading loop attached to an elongated gripping member and disposed within the eyelet of the anchor.
Figure 3C:
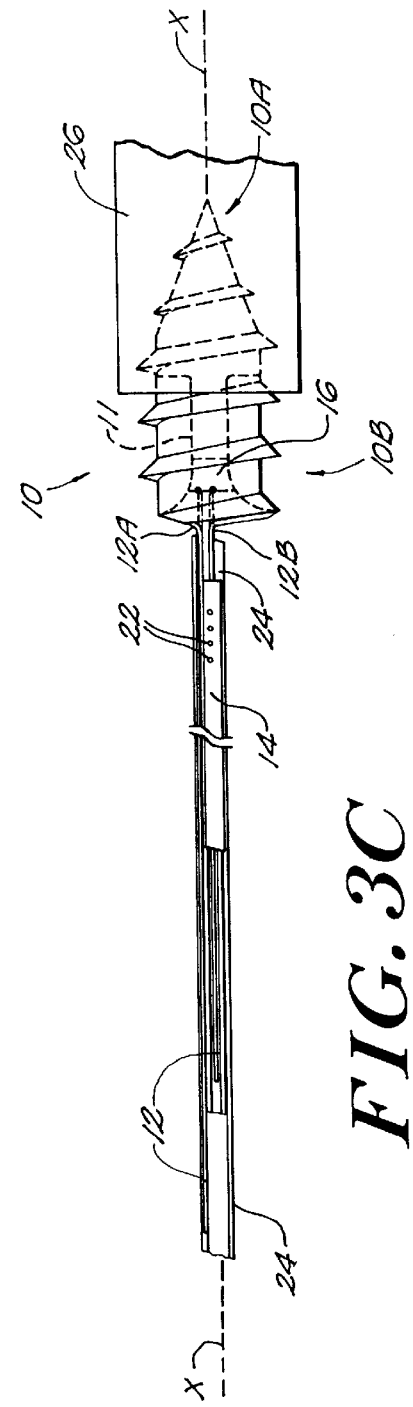
FIG. 3C is a side elevational view of the suture anchor in an anchor protecting sleeve, with the suture threading loop attached to an elongated gripping member and disposed within the eyelet of the anchor and also within an elongated sheath.

The suture anchor 10 is of a type known in the art which extends along a principal axis X between an anchor portion 10A at one end and a drive portion 10B at an opposite end, as shown in phantom in FIGS. 3B–3C. The suture anchor 10 is threaded along at least a portion of its length or otherwise adapted for secure engagement in bone and includes an eyelet 16 in the drive end 10B. The eyelet 16 is sufficiently large and suitably finished to accommodate one or more lengths of a suture or sections of soft tissue. In the illustrated embodiment, the suture anchor 10 is threaded over the entire length of the outside surface of the anchor from the anchor portion 10A to the drive portion 10B, as shown in FIGS. 3B–3C. The eyelet 16 of the illustrated suture anchor is the so-called "inverted" type which extends transversely through the body of the suture anchor near the drive end 10B of the anchor. As shown in FIG. 3B, the anchor 10 includes a pair of flat regions 11 extending on either side of the eyelet 16 in a direction parallel to the principal axis X of the anchor. The flat regions 11 permit a two-prong rotatable driver or extractor member to engage with the drive end 10B of the anchor, as detailed more fully below.

The suture threading loop 12, shown in FIG. 3A, extends from two proximate ends 12A and 12B and is disposed around a central void region 18. The loop includes two substantially parallel leg portions 20 which extend from the void region 18 to the gripping member 14.

The gripping member 14 is an elongated, substantially rigid member which is secured to, and extends from, a point at or near the proximal ends of the loop 12, such as by a crimp or spot weld 22. The loop 12 is positionable alongside the rigid gripping member 14, as shown in FIGS. 3B–3C, so that an elongated tubular sheath 24 can be disposed around, and frictionally engage with, both the loop 12 and the gripping member 14. The gripping member 14 acts as a wand to direct and manipulate the suture threading loop 12, which is pre-loaded into the eyelet 16 of the suture anchor 10 prior to installation of the suture anchor 10 into a bone. The gripping member 14 is elongated to facilitate handling of the suture threading loop and suture anchor and to bring the suture threading loop outside of the patient's body so that a suture can be relatively easily threaded through it and the eyelet of the suture anchor from outside of the patient's body.

When installed over the suture threading loop 12 and the elongated gripping member 14, the elongated sheath 24 preferably extends from a point near the proximal ends 12A, 12B of the loop to a point beyond the loop and the distal end 14A of the gripping member 14, as shown in FIGS. 2A–2B. The elongated sheath 24 is preferably made of a flexible, lightweight material, such as plastic, with a diameter which is sufficiently large to enclose the threading loop and elongated gripping member as they are disposed alongside one another without severely restricting movement of the sheath relative to the threading loop and gripping member.

In a preferred embodiment, a portion of the sheath 24 is compressed about the gripping member 14 and suture threading loop 12 therein, such as by controlled application of local heating to the sheath 24 with a heat gun, to establish frictional engagement between the sheath 24 and the gripping member 14 and threading loop 12. As will be detailed more fully below, this frictional engagement of the sheath with the gripper and threading loop prevents premature disengagement of the sheath 24 from the gripper 14 and threading loop 12.

As shown in FIG. 1 and explained in greater detail below, the end portion 24A of the elongated sheath 24 which extends beyond the loop 12 and gripping member 14 extends through an opening in a sidewall of a cannulated driver and is engageable with the driver at that end so that removal of the driver from the suture anchor after the anchor is installed effects a simultaneous removal of the elongated sheath, thereby exposing the suture threading loop and gripping member in preparation for threading of the suture anchor. Axial withdrawal of the driver from the suture anchor after the suture anchor is installed typically provides sufficient axial force to overcome the frictional engagement established between the sheath 24 and the gripping member 14 and threading loop 12 therein, so that the sheath can be removed with the driver.

As shown best in FIGS. 2B and 3A–3B, the loop 12 is preferably made of a resilient material, such as a wire, which is sufficiently rigid to maintain a loop shape even when the loop is temporarily collapsed or is otherwise partially flattened to fit alongside the gripping member 14 and/or within the elongated sheath 24. In a preferred embodiment, stainless steel is used as the material for the loop, although other materials meeting the above-described requirements are within the scope of the invention.

As shown in FIGS. 2A and 3B–3C, an anchor protector 26 can be inserted over the anchor portion 10A of the suture anchor 10 to facilitate handling of the anchor, which may relatively small and difficult to grasp without forceps, and to protect both the anchor portion 10A and anything which may come into contact with the anchor portion 10A prior to installation of the anchor into bone. The anchor protector 26 can be, for example, a sleeve of flexible or rigid tubing, such as plastic tubing, which slips over and frictionally engages with at least the anchor portion 10A of the anchor. Preferably, the anchor protector 26 extends beyond the end of the anchor portion 10A for a sufficient length to facilitate handling of the anchor, as shown in FIG. 2A. As detailed more fully below, the anchor protector 26 is designed for removable engagement with the suture anchor 10 and is retained on the suture anchor until just prior to installation of the anchor into bone.

Figure 4C:
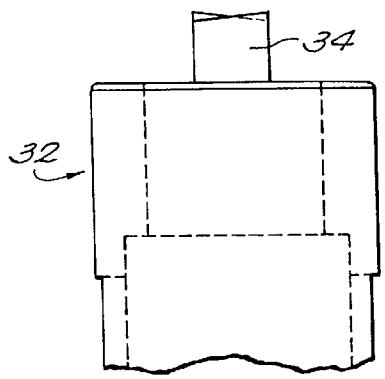
FIG. 4C is another side elevational view of the bit of FIG. 4A.
Figure 4D:
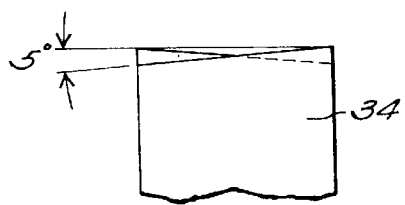
FIG. 4D is a detail view of the projection fingers of the bone-cutting drive bit illustrated in FIG. 4C.

The kit shown in FIG. 1 includes the suture anchor threading assembly described above, and a rotatable cannulated driver 28. The driver 28, shown in greater detail in FIGS. 4B and 5, comprises a cannulated shaft 30 extending along a principal axis Y between a first end 30A and a second end 30B. The first end 30A of the cannulated shaft is removably engageable with the drive end 10B of the suture anchor 10. In a preferred embodiment, the first end 30A of the cannulated shaft 30 is adapted to receive a bone-cutting drive bit 32, shown in FIGS. 4A–4D. According to the illustrated embodiment, the bit 32 includes two prong-like projections 34 which engage with the flat portions 11 of the suture anchor 10 to enable the anchor to be rotated and thus turned into or out of an installation site in a bone. As shown in FIG. 4D, the projections 34 are preferably chamfered or otherwise provided with sharpened bone-cutting edges to facilitate the formation of a countersunk hole in the bone for installation of the anchor into the bone. As shown in FIGS. 4C and 4D, in a preferred embodiment each projection 34 includes a 5 degree chamfer. The chamfers preferably extend in opposite directions, as shown in FIGS. 4C–4D, to facilitate entry of the bit 32 into the bone as the driver and bit are rotated.

The bone-cutting drive bit 32 is preferably permanently attached to the driver shaft, such as by laser welding. Alternatively, the bit can be removably attached to the driver shaft, such as with an interference fit or removable locking pins.

The cannulated shaft 30 of the driver 28 includes a central canal 36, shown in FIG. 5, which is sufficiently large to permit passage therethrough of the elongated sheath 24 containing the suture threading loop 12 and the elongated gripping member 14. As shown in FIGS. 1 and 4B, a port 38 located in a sidewall of the cannulated shaft 30 provides an exit aperture through which a distal end 24A of the elongated sheath 24 passes.

Figure 9A:
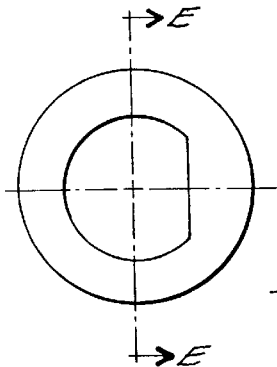
FIG. 9A is an axial view of a first end of an annular element which fits over the cannulated driver shaft and is engageable with the elongated sheath.
Figure 9B:
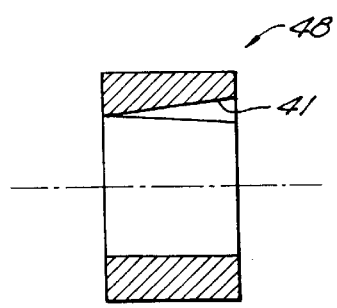
FIG. 9B is a sectional view of the annular element of FIG. 9A along section lines E—E.
Figure 9C:
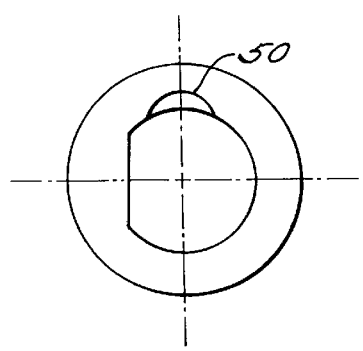
FIG. 9C is an axial view of an opposite end of the annular element.

The port 38 is located at a distance from the first end 30A of the cannulated shaft 30 which is less than the length of the elongated sheath 24. As a result, the distal end portion 24A of the sheath 24 extends through the port 38 and can engage frictionally with an annular element 48 which is disposed around the cannulated shaft 30, as shown in FIG. 1 and in greater detail in FIGS. 9A–9C. The annular element 48 can be made of, for example, plastic or other lightweight material and includes a variable-height recess 50 along one side of its inner diameter, as shown in FIGS. 9B–9C. The variable-height recess 50 is sufficiently large to permit the distal end 24A of the elongated sheath 24 to be held frictionally within the annular element 48 and against the outside of the cannulated shaft 30 without crushing or otherwise damaging the elongated sheath 24. The annular element 48 is slidable along a portion of the cannulated shaft 30 in the direction of arrows 42 in FIG. 1 for selective engagement with the distal end 24A of the elongated sheath 24.

When the end 24A of the sheath 24 is engaged with the annular element 48, and as a result of the compression of a portion of the sheath around the gripping member and threading loop, sufficient tension is applied to the gripper 14 and threading loop 12, and thus to the suture anchor 10, to maintain the suture anchor 10 firmly seated in the cutting drive bit 32 so that the anchor alignment can be controlled and maintained during its installation. After the suture anchor 10 has been installed, retraction of the driver 28 transmits sufficient axial force to overcome the frictional engagement between the sheath 24 and the gripping member 14 and threading loop 12 therein resulting from selected compression of the sheath around those elements. Withdrawal of the driver from the suture anchor after installation of the anchor into bone simultaneously retracts the elongated sheath 24 with the driver to expose the suture threading loop 12 and elongated gripper member 14.

Figure 7A:
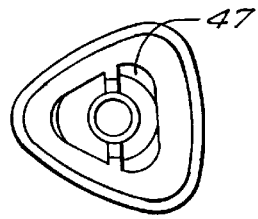
FIG. 7A is an axial view of the handle.
Figure 7B:
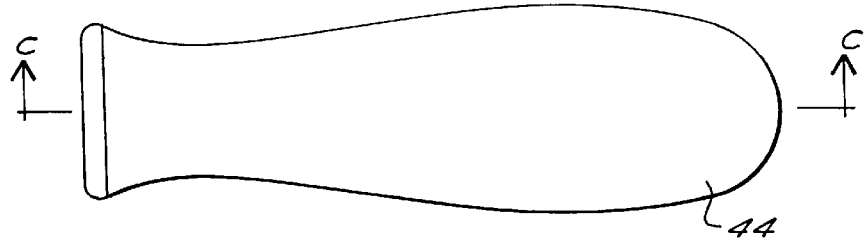
FIG. 7B is a side elevational view of the handle.
Figure 7C:
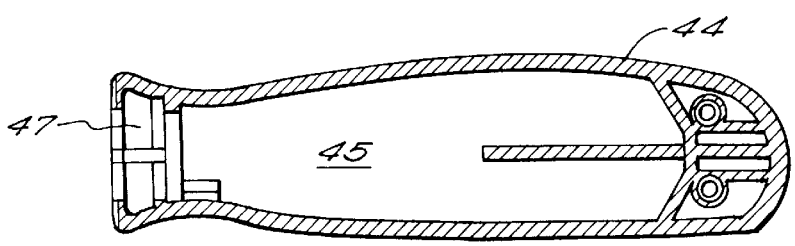
FIG. 7C is a sectional view of the handle of FIG. 7B along section lines C—C.
Figure 8A:
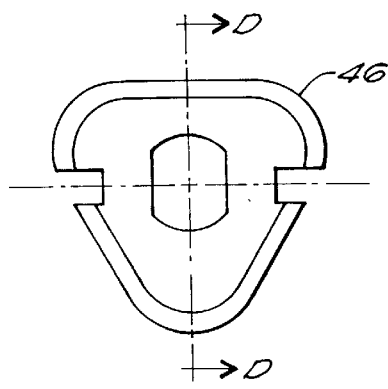
FIG. 8A is an axial view of an anti-rotation sleeve which fits over the shaft of the driver and within the handle, as illustrated in FIG. 1.
Figure 8B:
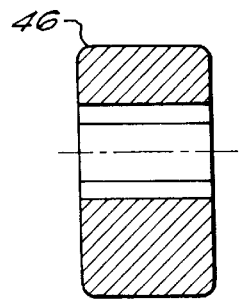
FIG. 8B is a sectional view of the anti-rotation sleeve of FIG. 8A along section lines D—D.

A handle 44 is adapted for releasable engagement with the second end 30B of the driver 28, as shown in FIG. 1 and in greater detail in FIGS. 7A–7C. The handle 44 includes a central void region 45 extending axially therethrough to accommodate a portion of the shaft 30. The handle 44 is preferably constructed of a lightweight material, such as plastic, and preferably is adapted to receivingly engage with an anti-rotation sleeve element 46, shown in FIGS. 1 and 8A–8B, which is insertable into an opening in the handle and is adapted for frictional engagement with the cannulated shaft 30 of the driver 28. In the illustrated embodiment, the anti-rotation sleeve element 46 has a triangular cross-section, as shown in FIG. 8A, and fits within a corresponding triangular bore 47 in the handle 44. This non-circular design facilitates the secure engagement of the sleeve 46 in the handle 44 and permits the handle 44 and driver 28 to be rotated together in both the clockwise and counter-clockwise directions without slipping relative to one another.

The second end 30B of the cannulated shaft 30 fits within the void region 45 of the handle 44, as shown in FIGS. 1 and 7C. The driver 28 can be easily inserted into the handle by pushing it axially into the void region 45 and adjusting the position of the anti-rotation sleeve element 46 along the driver shaft 30 until the sleeve element 46 engages with the correspondingly-shaped opening 47 in the handle. Similarly, the driver 28 can be easily removed from the handle 44 by pulling it axially from the handle until the sleeve element 46 releases from the handle.

Figure 6:
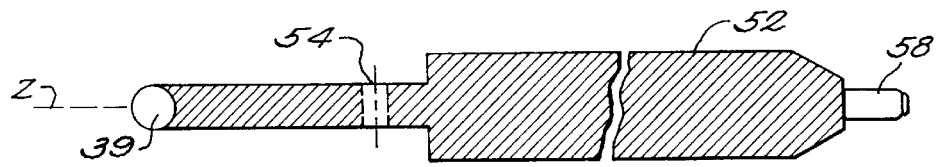
FIG. 6 is a sectional view of the anchor extraction member of FIG. 5 along section lines B—B.

The kit can further include an anchor extractor member 52, shown in FIGS. 1, 5 and 6, which is disposed at the second end 30B of the cannulated shaft 30 of the driver 28. The anchor extractor member 52 is adapted for releasable engagement with the drive end 10B of the suture anchor 10 and is designed to facilitate removal of the suture anchor from its installation site in a bone. The anchor extractor member 52 extends along a principal axis Z and includes a through hole 54 near a proximal end 52A thereof. A corresponding through hole 56 is located in the shaft 30 of the driver 28. The through holes 54, 56 are adapted to receive a pin for securing the anchor extractor member 48 within the shaft 30. In a preferred embodiment, the distal tip 52A of the anchor extractor member 52 includes a pair of fingerlike projections 58 which extend into and engage with the flat regions 11 near the eyelet 16 of the anchor 10. Counter-clockwise rotation of the extractor member 52 in the drive end of the suture anchor 10 which has been installed into a bone disengages the anchor from the bone and permits it to be loosened or removed.

In a preferred embodiment, the anchor extractor member 52 includes a wedge-shaped end 39 which can act as a guide for the end of the elongated sheath 24 (indicated by dashed line 41 in FIG. 5) to facilitate its passage through the port 38.

In a preferred embodiment, the anchor extractor member 52 is adapted to fit within the void region 45 of the handle 44 in the same manner in which as the drive bit end of the driver 28 fits within the handle. With this design, the driver 28 can include a bone-cutting drive bit 32 at one end 30A and an anchor extractor member 52 at an opposite end 30B, and either end of the driver 28 can be engaged securely with the handle 44.

The shaft 30 preferably includes a flat region 49 at the location of the anti-rotation sleeve element 46 which permits the axial position of the anti-rotation sleeve to be varied along the shaft. When the shaft is withdrawn from the handle after installation of a suture anchor in bone and in preparation for extraction of the suture anchor, the anti-rotation sleeve 46 can be moved axially along the length of the flat region 49 to locate it in the desired position on the shaft to secure the driver shaft within the handle.

The driver and extractor member, as well as the suture threading loop, are all made in a variety of sizes to accommodate the various sizes of suture anchor which are used in surgical procedures.

A suture anchor can be conveniently installed into a bone and threaded with a suture or a section of tendon or other soft tissue after installation according to the following method. First, a suture anchor of the appropriate size is selected. The suture anchor may be provided with an anchor protector already installed on it to protect the anchor and facilitate its handling. A corresponding driver and extractor member which will fit the suture anchor are then selected. An anti-rotation sleeve and an annular element are disposed around the driver shaft. A handle which is suitable for engaging the driver shaft and extractor member is then selected. The handle is assembled to the driver shaft by sliding the handle over the driver shaft and aligning the anti-rotation sleeve on the shaft with the corresponding opening in the handle, with the cutting drive bit end of the driver exposed and the anchor extractor member, if provided, disposed within the interior of the handle.

The suture threading loop may be flattened and caused to extend alongside the elongated gripping member. Both the loop and the gripping member are then inserted into the elongated sheath, the distal end of which extends for approximately an inch beyond the ends of the loop and gripping member within the sheath. The sheath is controllably compressed about a portion of the gripping member and threading loop therein to establish a frictional engagement between the sheath and those elements inside the sheath.

The preloaded suture anchor is then assembled to the driver by holding the anchor protector and inserting the suture threading loop, the attached elongated gripping member and the elongated sheath surrounding them into the cannulated shaft from the drive bit end. The flat regions of the suture anchor are then aligned with the fingerlike projections on the bone-cutting drive bit to engage and fully seat the anchor with the bit. The distal end portion of the elongated sheath containing the suture threading loop and elongated gripping member should extend through the port in the cannulated shaft. The annular element can then be slid over the distal portion of the sheath to engage it against the shaft. This operation also secures the suture anchor to the driver.

The anchor protector can now be removed from the anchor by twisting it off of the anchor, in preparation for installation of the anchor into a bone.

The tip of the anchor is then placed substantially perpendicular to the bone into which it is to be installed. The driver is rotated clockwise by the handle with application of constant axial pressure. Care should be taken to keep the anchor perpendicular to the bone to prevent premature dissociation of the anchor from the driver. The driver is rotated in a clockwise direction until the anchor disengages from the cutting bit and is fully installed into the bone. After disengagement, the driver can be pulled away from the anchor, thereby removing the elongated sheath and exposing the suture threading loop and elongated gripping member. The elongated sheath will be retained with the driver shaft and annular element and can be discarded. The driver can be reused to install another suture anchor.

Once the suture threading loop is exposed, a suture or section of soft tissue, such as a tendon, can be threaded through the eyelet of the installed anchor by inserting the suture or soft tissue section through the threading loop and then pulling the elongated gripping member and attached threading loop through the eyelet. The suture or soft tissue section will be pulled through the eyelet with the threading loop. Care should be taken to provide a sufficient length of suture or soft tissue section so that the anchor can be threaded properly. The suture threading loop and elongated gripping member can be discarded after the suture or soft tissue section is threaded through the eyelet of the anchor.

To loosen and/or remove the threaded suture anchor from the bone, the driver shaft is removed from the handle and reversed to expose the anchor extractor member. The driver is then reassembled to the handle with the anchor extractor member exposed for operation. The anti-rotation sleeve is positioned in the desired axial location along the shaft to ensure secure engagement of the shaft in the handle. Once the driver is reassembled, the fingerlike projections of the extractor member are engaged with the flat regions of the suture anchor. The extractor member is rotated counter-clockwise by the handle to loosen and/or remove the anchor from the bone.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description. All changes that come within the meaning and range of the equivalency of the claims are therefore intended to be embraced therein.

We claim:

1. A self-threading suture anchor assembly comprising:
   A. a suture anchor extending along a principal axis and having an eyelet at a drive end and an anchor portion at an end opposite the drive end; and
   B. an elongated suture threading loop extending from two proximal loop ends through the eyelet of the suture anchor and having an elongated, substantially rigid gripping member extending from said proximal ends of said loop, wherein said loop is positionable adjacent to and alongside said gripping member, and further comprising an elongated sheath disposed around and frictionally engaged with said loop and said gripping member, wherein said elongated sheath extends from a point near said proximal ends of said loop and said gripping member to a point beyond said loop and said gripping member.

2. A self-threading suture anchor assembly according to claim 1, wherein said elongated suture threading loop is sufficiently rigid to maintain a loop shape, and wherein said loop is disposed about a void region and includes two substantially parallel leg portions extending from said void region to said gripping member.

3. A self-threading suture anchor assembly according to claim 2, wherein said loop is positionable adjacent to and alongside said gripping member, and further comprising an elongated sheath disposed around and frictionally engaged with said loop and said gripping member.

4. A self-threading suture anchor assembly according to claim 3, wherein said elongated sheath extends from a point near said proximal ends of said loop and said gripping member to a point beyond said loop and said gripping member.

5. A self-threading suture anchor kit, comprising:
   A. a self-threading suture anchor assembly, comprising:
      i. a suture anchor extending along a principal axis and having an eyelet at a drive end and an anchor portion at an end opposite the drive end; and
      ii. an elongated suture threading loop extending from two proximal ends thereof through the eyelet of the suture anchor and having an elongated, substantially rigid gripping member extending from said proximal ends of said loop,
   wherein said elongated suture threading loop is positionable adjacent to and alongside said elongated gripping member and is sufficiently rigid to maintain a loop shape, and wherein said loop is disposed about a void region and includes two substantially parallel leg portions extending from said void region to said gripping member; and
      iii. an elongated sheath disposed around and frictionally engaged with said loop and said gripping member, said loop extending from a point near said proximal ends of said loop and said gripping member to a point beyond said loop and said gripping member; and
   B. a rotatable driver comprising a cannulated shaft extending along a principal axis between first and second ends, said first end being removably engageable with said drive end of said suture anchor, said cannulated shaft defining a central canal adapted for passage of said elongated sheath therethrough and including a port in a sidewall of said cannulated shaft, wherein the distance between said port and said first end of said cannulated shaft is less than the length of said elongated sheath.

6. A self-threading suture anchor kit according to claim 5, further comprising an annular element disposed around said cannulated shaft between said port and said first end of said cannulated shaft, said annular element being adapted for frictional engagement with said elongated sheath.

7. A self-threading suture anchor kit according to claim 5, further comprising a handle adapted for releasable engagement with said second end of said cannulated shaft.

8. A self-threading suture anchor kit according to claim 5, further comprising a bone-cutting drive bit engageable with said first end of said cannulated shaft, said bit including a pair of axially-extending prong-like projections adapted for releasable engagement with said drive end of said suture anchor.

9. A self-threading suture anchor kit according to claim 8, wherein said prong-like projections of said cutting bit include chamfered leading edges adapted for cutting bone.

10. A self-threading suture anchor kit according to claim 8, further comprising a handle adapted for releasable engagement with said second end of said cannulated shaft.

11. A self-threading suture anchor kit according to claim 5, further comprising an anchor extractor member disposed at said second end of said cannulated shaft, said extractor member being adapted for releasable engagement with said drive end of said suture anchor.

12. A self-threading suture anchor kit according to claim 11, further comprising a handle adapted for releasable engagement with said first end of said cannulated shaft.

13. A self-threading suture anchor kit according to claim 11, wherein said anchor extractor member includes a wedge-shaped end disposed within said cannulated shaft near said port, said wedge-shaped end being adapted for guiding said elongated sheath in said canal toward said port.

14. A self-threading suture anchor kit according to claim 5, wherein said proximal ends of said loop are secured to said elongated gripping member near a proximal end of said gripping member.

* * * * *